(12) United States Patent
Fischer et al.

(10) Patent No.: US 8,103,609 B2
(45) Date of Patent: Jan. 24, 2012

(54) KNOWLEDGE-BASED INPUT REGION OF INTEREST DEFINITION FOR PHARMACOKINETIC MODELING

(75) Inventors: Alexander Fischer, Aachen (DE); Lothar Spies, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 979 days.

(21) Appl. No.: 12/067,481

(22) PCT Filed: Sep. 13, 2006

(86) PCT No.: PCT/IB2006/053265
§ 371 (c)(1),
(2), (4) Date: Mar. 20, 2008

(87) PCT Pub. No.: WO2007/034378
PCT Pub. Date: Mar. 29, 2007

(65) Prior Publication Data
US 2008/0228686 A1 Sep. 18, 2008

Related U.S. Application Data

(60) Provisional application No. 60/718,896, filed on Sep. 20, 2005.

(51) Int. Cl.
G06F 17/00 (2006.01)
G06N 5/02 (2006.01)

(52) U.S. Cl. ............................................. 706/46

(58) Field of Classification Search .................. None
See application file for complete search history.

(56) References Cited

U.S. PATENT DOCUMENTS

| 4,643,891 | A | * | 2/1987 | Panek | .................. | 424/1.61 |
| 2003/0048937 | A1 | * | 3/2003 | Gullberg et al. | .............. | 382/131 |
| 2003/0144798 | A1 | | 7/2003 | Gardner | | |
| 2004/0023211 | A1 | | 2/2004 | Groen | | |
| 2004/0107084 | A1 | | 6/2004 | Arakelyan | | |
| 2004/0242994 | A1 | | 12/2004 | Brady | | |

FOREIGN PATENT DOCUMENTS

JP 2003275302 9/2003

OTHER PUBLICATIONS

Ichise et al. "Linearized Reference Tissue Parametric Imaging Methods: Application to [11C]DASB Positron Emission Tomography Studies of the Serotonin Transporter in Human Brain", Journal of Cerebral Blood Flow & Metabolism, 23:1096-1112.*
Ahn, Ji Young et at "Quantification of Regional Myocardial Blood Flow Using Dynamic H215O PET and Factor Analysis" J Nucl Med, vol. 42, No. 5, pp. 782-787, May 2001.

(Continued)

*Primary Examiner* — Jeffrey A Gaffin
*Assistant Examiner* — Li-Wu Chang (57) ABSTRACT

A system, apparatus, and method are based on a priori knowledge of the shape of the input function for defining an input region-if-interest (ROI) in pharmacokinetic modeling. Kinetic parameter estimation requires knowledge of tracer input activity and the present invention provides an automatic way to define an ROI for estimation of an input function that takes into account a priori knowledge of the shape of the input function based on an administered dose.

12 Claims, 5 Drawing Sheets

OTHER PUBLICATIONS

Liptrot, Matthew et al "Cluster Analysis in Kinetic Modelling of the Brain: A Noninvasive Alternative to Arterial Sampling" Neuroimage, vol. 21, No. 2, Feb. 2004, pp. 483-493.

Feng, (David) Dagan, "Information Technology Applications in Biomedical Functional Imaging", IEEE Transactions on Information Technology in Biomedicine, vol. 3, No. 3, Sep. 1999.

Guo, Hongbin et al "Clustering Huge Data Sets for Parametric PET Imaging" Science Direct, BioSystems, vol. 71, 2003, pp. 81-92.

Kim, Jinman et al "Automatic 3D Temporal Kinetics Segmentation of Dynamic Emission Tomography Image Using Adaptive Region Growing Cluster Analysis" 2002 IEEE Nuclear Science Symposium Conference Record, vol. 3, Nov. 2002, pp. 1580-1583.

Lee, Jae Sung et al "Blind Separation of Cardiac Components and Extraction of Input Function from H2 15O Dynamic Myocardial PET Using Independent Component Analysis" The Journal of Nuclear Medicine, vol. 42, No. 6, Jun. 2001.

Sokal, Robert R. et al "A Statistical Method for Evaluating Systematic Relationships" Univ. Kansas, Science Bulletin, VOl. vol. 38, No. 22, Mar. 1958, pp. 1409-1438.

Tsuchida, Tatsuro et al "Noninvasive Measurement of Cerebral Metabolic Rate of Glucose using Standardized Input Function" Journal of Nuclear Medicine, Society of Nuclear Medicine, vol. 40, No. 9, pp. 1441-1445.

Wong, Koon-Pong et al "Segmentation of Dynamic PET Images Using Cluster Analysis" IEEE Transactions on Nuclear Science, vol. 49, No. 1, Feb. 2002.

Zhou, Y. et al "Model Fitting with Spatial Constraint for Parametric Imaging in Dynamic PET Studies" PhD Thesis, UCLA, Biomedical Physics 2000.

\* cited by examiner

KNOWLEDGE-BASED INPUT REGION OF INTEREST DEFINITION FOR PHARMACOKINETIC MODELING

The present invention relates to a system, apparatus and method for defining an input region-of-interest (ROI) for estimating parameters of a kinetic model/input function from a 4-dimensional data set comprising a series of tracer activity measurements distributed over time and space. More specifically, the present invention provides an automatic way to define the ROI that takes into account a priori knowledge of the shape of the input function based on an administered dose.

Pharmacokinetic modeling estimates parameters of a kinetic model from a series of tracer (radioactively labeled imaging agent) activity measurements (e.g., by positron emission tomography). Since the model describes a biological process its parameters have a direct functional interpretation (e.g., hypoxia for the tracer F-Fluoromisonidazole (FMISO)) that is of diagnostic value. The measurements represent the activity distribution in time and space in the form of a four-dimensional (4D) data set. The kinetic parameter estimation procedure requires knowledge of the tracer input activity. This input activity can either be measured invasively or it can be estimated from the data in a preprocessing step.

The estimation problem can be solved efficiently if the model and its input are described analytically. When using medical imaging devices such as computed tomography (CT), magnetic resonance (MR), positive emission tomography (PET), single photon emission computed tomography (SPECT), and ultra sound (US) to display functional/morphological properties of a patient under study, either a number of static scans or a contiguous time series of dynamic scans, are recorded. To obtain the medical information of interest encoded in these images, in certain applications a compartmental analysis of the underlying chemical, biological and physiological processes must be accomplished. To take advantage of the maximal resolution, which the imaging devices can provide, this analysis must be done on a per-voxel basis.

Typically parameterized functions (often sums of exponential terms) are fitted to the averaged data over the ROI, e.g., an artery or the left ventricular blood pool, in order to obtain an analytical input representation. The ROI in the data used for the estimation of the input function is important in order to obtain a proper input-function representation.

This system, apparatus and method of the present invention provide an automatic way to define the input region-for-interest (ROI) for estimation of an input function by taking into account a priori knowledge of the shape of the input function based on an administered dose. This results in reduction of the amount of manual interaction and dependence on an operator in the evaluation of dynamic procedures.

Non-invasive input function estimation is an important component of pharmacokinetic modeling when the goal is routine clinical usage. Pharmacokinetic modeling estimates the parameters of a kinetic model from a series of activity measurements of a radio-labeled imaging agent, obtained by an imaging technique such as PET. Estimation of the kinetic parameter requires an estimation of the input activity of the imaging agent. One way to estimate the input function is to extract it from a properly selected region in the measured data, i.e., a properly selected input ROI. This requires a reasonable ROI to be present in the data and its careful delineation. That is, the ROI in the data used for the input function estimation is important in order to obtain an accurate representation of the input function. ROI definition/delineation has been a time-consuming and operator-dependent task, and, therefore, automatic techniques for ROI definition/delineation, such as the present invention, that require minimal manual interaction are preferred. By using a priori data in the ROI definition/delineation for input function estimation, the present invention reduces the amount of manual interaction and operator dependence.

Currently, several automatic techniques are employed:

1. Factor Analysis is employed to address the ROI definition problem on 15-O water perfusion images that suffer from strong spill-over effects due to the tracer characteristics, see, e.g., Ji Young Ahn, et. al., "Quantification of Regional Myocardial Blood Flow Using Dynamic H215-O PET and Factor Analysis," *J Nucl Med*, vol. 42, no. 5, pp. 782-787, May 2001. Factor Analysis is available in the commercially available kinetic analysis package PMOD, see, e.g., the home page of PMOD Technologies LTD entitled "Biomedical Image Quantification and Kinetic Modeling Software," available on the World Wide Web at pmod.com/technologies/index.html, Aug. 4, 2005.

However, drawbacks remain such as the lack of physiological meaning in the factor images and the sensitivity of the factor analysis to the limited spatial and time resolutions as well as the level of noise in the data to be analyzed.

2. Independent Component Analysis as a source separation technique is employed to tackle the ROI definition problem described in paragraph 1 above, see, e.g., J. S. Lee, et. al., "Blind Separation of Cardiac Components and Extraction of Input Function from $H_2$15-O Dynamic Myocardial PET Using Independent Component Analysis," *J Nucl Med*, vol. 42, no. 6, pp. 938-943, June 2001. This approach is an extension of the previously discussed factor-analysis approach but addresses the noise problem. The data is transformed into independent components where the ROI definition is done automatically and is more feasible than one done with the original data. The principal issues with regard to resolution and interpretability remain.

3. Cluster analysis uses a standard (K means) clustering algorithm to group together those voxels from the data having similar time activity curves (TACs), see M. Liptrot, et. al., "Cluster Analysis in Kinetic Modeling of the Brain: A Non-Invasive Alternative to Arterial Sampling," *Neuroimage*, vol. 21, pp. 483-491, 2004. It has been applied to neurological problems where the ROI-based approaches using arteries suffer from the limited spatial resolution in nuclear medicine and the small size of the arteries in the images. The ROIs obtained in this fashion are functional rather than spatial ones.

Figure 5A:
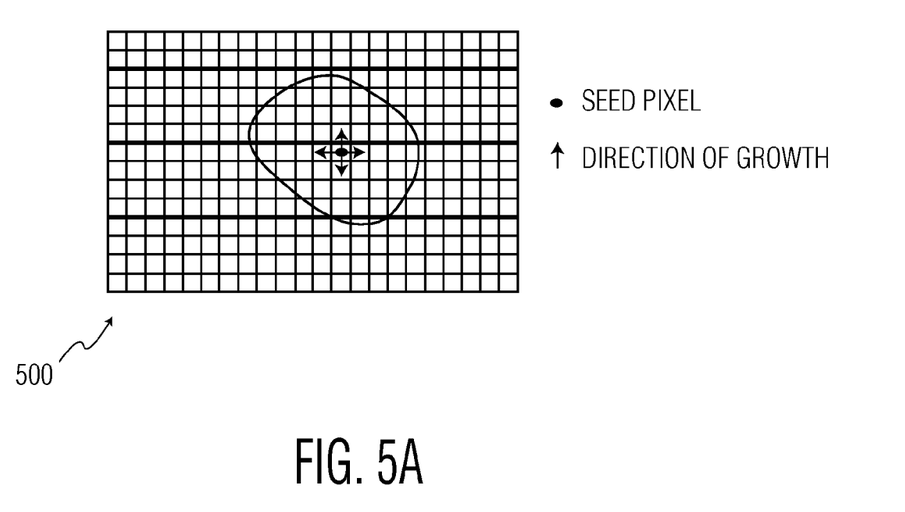
FIG. 5 illustrates an example of region growing.
Figure 5B:
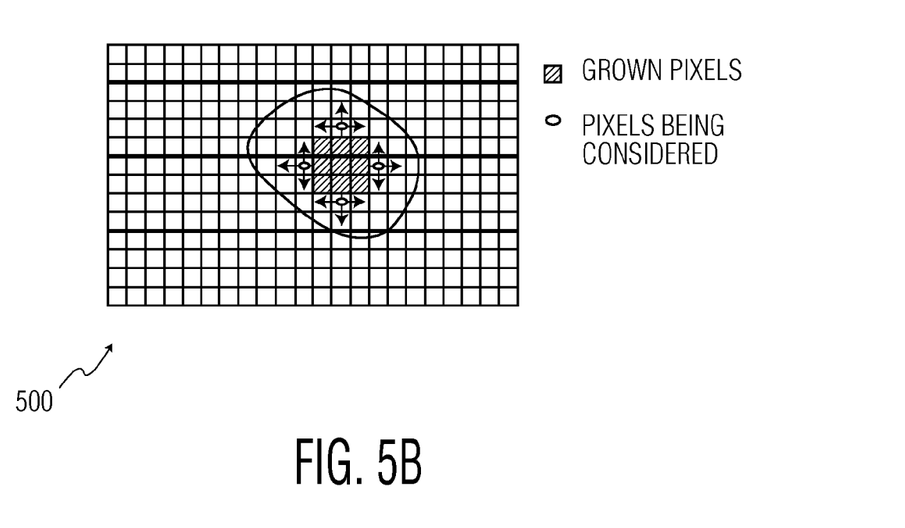

4. Region growing based on a seed point (manually defined or automatically chosen) is another technique in common use in which the process is started by choosing an arbitrary seed pixel and comparing it with neighboring pixels (see FIG. 5). A region is grown around the seed pixel by adding in neighboring pixels that are similar, increasing the size of the region. When the growth of one region stops, another seed pixel is chosen that does not yet belong to any region and the growing process is repeated. The selecting-growing process is iterated until all pixels belong to some region. Region-growing methods often give very good segmentations that correspond well to the observed edges. However, starting with a particular seed pixel and letting a region grow completely before trying other seeds biases the segmentation in favor of the regions that are segmented first and can have several undesirable results:

the current region dominates the growth process—ambiguities around edges of adjacent regions may not be resolved correctly;

different choices of seeds may give different segmentation results; and problems can occur if the (arbitrarily chosen) seed point lies on an edge.

To counter the above problems, simultaneous region growing techniques have been developed:
- similarities of neighboring regions are taken into account in the growing process;
- no single region is allowed to completely dominate the process;
- a number of regions are allowed to grow at the same time;

Similar regions will gradually coalesce into expanding regions. However, control of these methods may be quite complicated but efficient methods have been developed. On the positive side they are easy and efficient to implement on parallel computers.

Automatic or blind methods, such as those as discussed above, work to some extent in the presented scenarios, but their convergence to a proper and reasonable solution is not guaranteed.

The present invention uses a priori knowledge in the ROI definition for non-invasive input function estimation. The present invention uses the a priori knowledge to define shape characteristics of the input time activity curve (TAC) such as the peak size. The a priori knowledge that is exploited by the present invention includes the following:
- tracer characteristics and the administered dose;
- patient weight and blood volume (probably estimated from the weight); and
- scanner characteristics.

Based on the a priori knowledge and the parameters, the present invention computes a "reference TAC" and at least one major parameter of the computed "reference TAC." At least one major parameter of the "reference TAC" includes peak size and width. Using the computed "reference TAC," a clustering or region-growing algorithm is selected and steered to define an ROI. Cluster algorithms and the comparison to a "reference TAC" need a distance measurement for TACs. The present invention employs any one of a collection of distance measurements such as those provided by H. Guo, et. al., "Clustering huge data sets for parametric pet imaging," *Biosystems*, vol. 71, no. 1-2, pp. 81-92, 2003. In a preferred embodiment, these distance measures are defined as follows:

Assume that $d(x, y)$ is a measurement of the dissimilarity between the multivariable vectors x and y. For example, a typical choice would be the usage of $$d(x, y) = \left( \sum_{l=1}^{n} |(x_l - y_l)w_l|^p \right)^{1/p}$$

a weighted Minkowski p-norm which satisfies the mathematical requirements for a norm, and where the choice $w_l=1$ for all $l$ would suppose that each feature $x_l$ has equal significance. For p=2 this is the weighted sum of squares, or Euclidean distance, and for p=1 this is the weighted Manhattan norm. This distance may be calculated element-wise, i.e., for all elements in a given cluster as compared to all elements in another cluster, or with respect to a representative element of a cluster, such as the cluster centroid. The hierarchical centroid linkage (HCL), see R. R. Sokal et. al., "A Statistical Method for Evaluating Systematic Relationships," Univ. Kansas Sci. Bull. 38, pp. 1409-1438 (1958), uses the centroid $\mu_l$ for group l as the representative group vector and the distance between clusters is given by the distance between the group vectors, $D_{IJ}=d(\mu_I, y_J)$. The distance of a single point to a single cluster is $d(\mu_I, y_J)$. Y. Zhou, "Model Fitting with Spatial Constraint for Parametric Imaging in Dynamic PET Studies," Ph.D. thesis, UCLA, Biomedical Physics, (2000) uses HAL, where the average distance between clusters I and J, of sizes $n_I$ and $n_J$, respectively, given by $$D_{IJ} = \frac{1}{n_I n_J} \sum_{i \in I} \sum_{j \in J} d(x_i, y_j)$$

is used to measure an average distance with respect to all pairs of elements (Sokal et. al., supra).

For PET, it is imperative that weighing is included in order to account for the difference in the SNR of the different time frames due to the increasing time windows used in functional PET. Therefore, the elements $x_l$ are weighed with $w_l = t_l$, where $t_l$ is the width of the $l^{th}$ time window. FIG. 2 illustrates clustering of five clusters for slice 16 of an FDG-PET image of a healthy individual with different distances. From right to left and top to bottom, these are: (a) Manhattan distance, (b) Euclidean distance, (c) weighted Manhattan distance and (d) weighted Euclidean distance.

In an alternative embodiment, the "reference TAC" is used as a diagnostic (post-) check on the automatically extracted regions from above.

The present invention incorporates a priori knowledge in the definition for the input function in pharmacokinetic modeling. Thereby, the present invention:
- increases robustness through an additional constraint based on the a priori knowledge that can prevent automatic or blind techniques from producing non-plausible solutions; and
- serves as a diagnostic check on automatic or blind techniques in order to detect problems or failures requiring manual interaction.

It is to be understood by persons of ordinary skill in the art that the following descriptions are provided for purposes of illustration and not for limitation. An artisan understands that there are many variations that lie within the spirit of the invention and the scope of the appended claims. Unnecessary detail of known functions and operations may be omitted from the current description so as not to obscure the present invention.

The inclusion of a priori knowledge, in accordance with the present invention, in the input estimation step of pharmacokinetic modeling increases robustness and allows a higher level of automation. This streamlines the workflow and reduces the amount of manual interaction for the analysis of a dynamic procedure with kinetic modeling which is mandatory for routine clinical usage.

Figure 3:
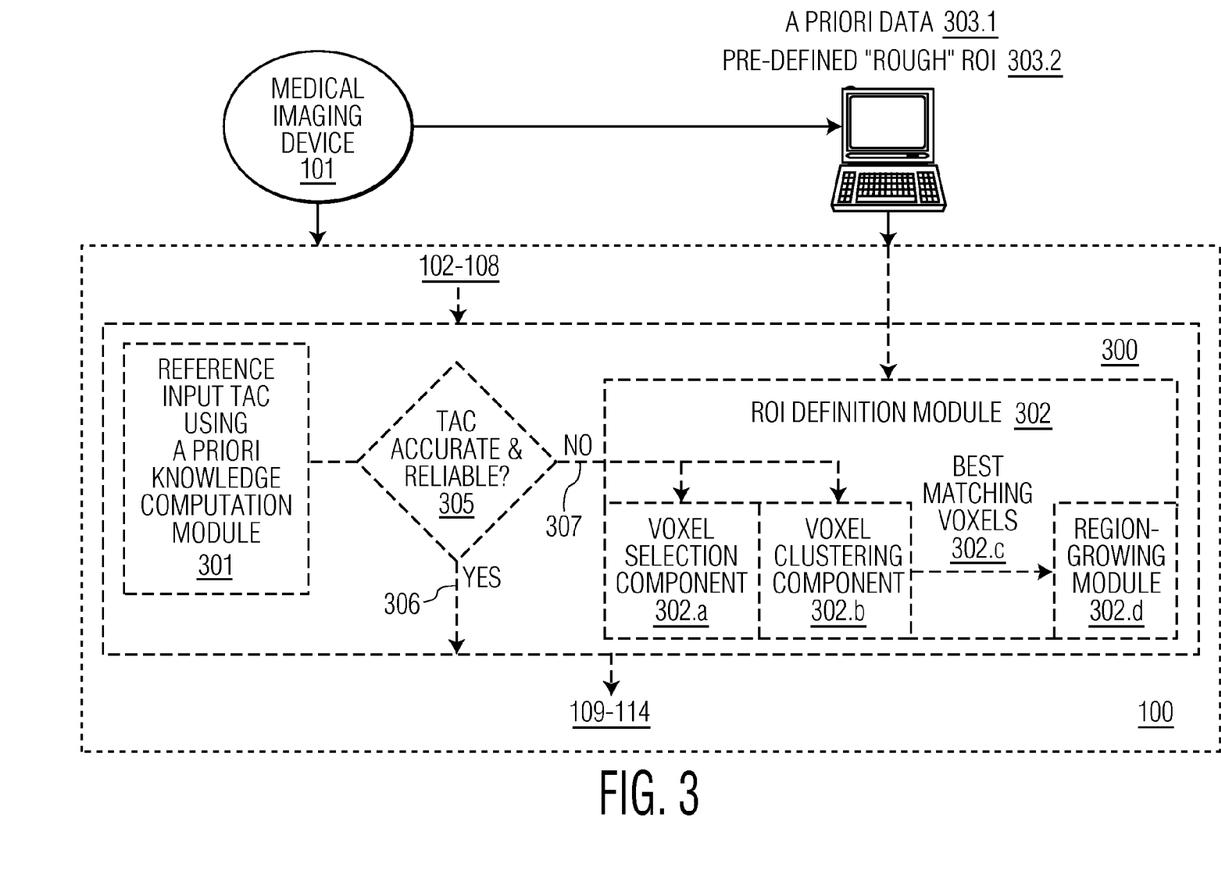
FIG. 3 illustrates an apparatus according to the present invention for a knowledge-based definition of a region-of-interest.

Referring now to FIG. 3, according to a preferred embodiment, the inclusion of a priori knowledge in the ROI definition for input-function estimation is accomplished by performing the following steps:

1. a reference input TAC computation module 301—computing a "reference input TAC" reflecting the a priori knowledge as stated above by performing the following substeps:

a. providing an administered tracer dose and a scanner sensitivity 301.*a*;
b. deriving an estimate and input peak size based on the provided dose and sensitivity 301.*b*;
c. providing an infusion protocol and a blood volume 301.*c*;
d. estimating at least one of a peak width and tail width with the use of a combination of the provided protocol and volume 301.*d*;
e. defining the "reference input TAC" 301.*e* by using at least one of the estimated peak and tail to perform a step selected from the group consisting of the following steps:
  i. parametrically characterizing the "reference input TAC" 301.*e.i*; and
  ii. constructing a full representation of the "reference input TAC" 301.*e.ii*.

Figure 4:
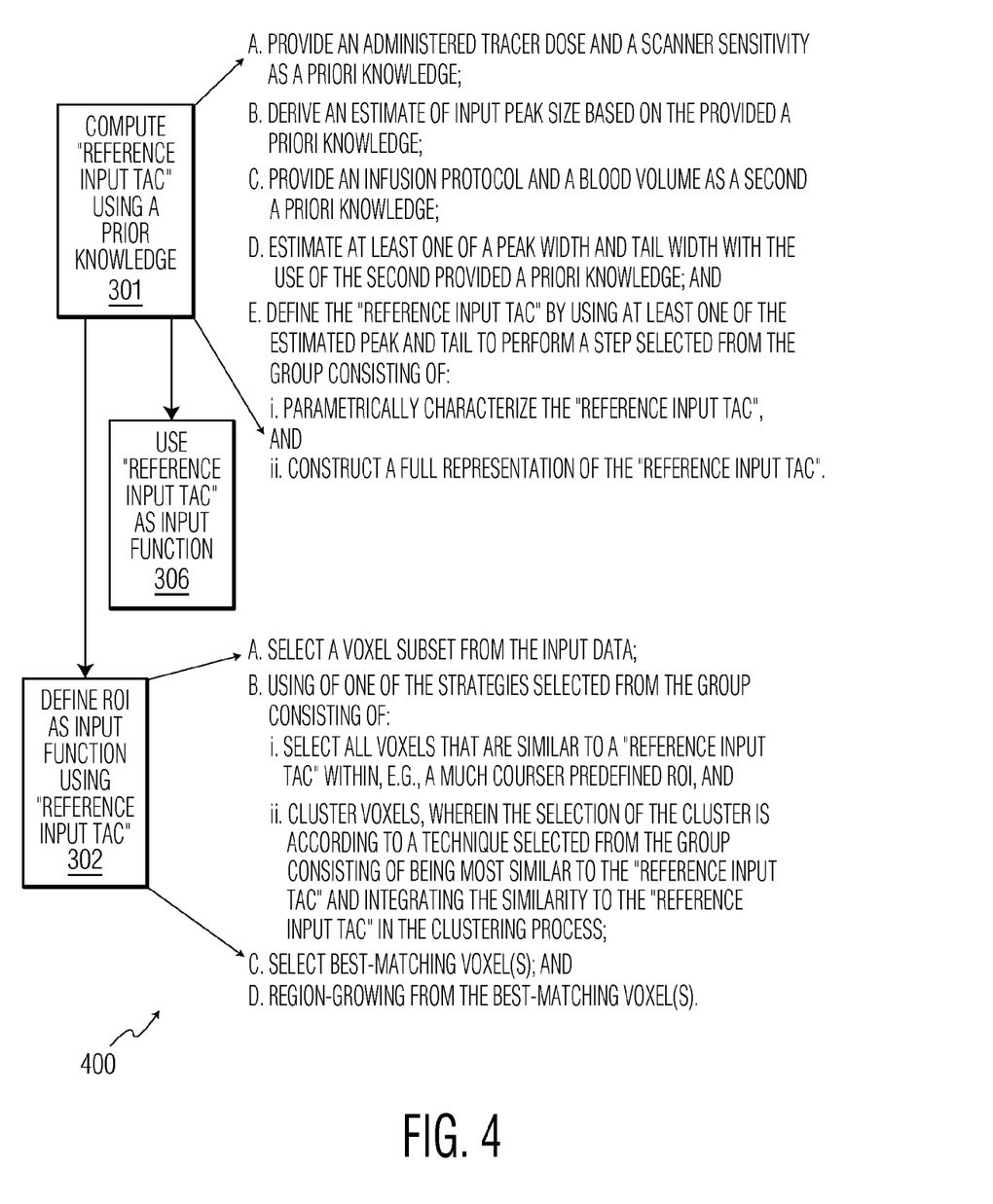
FIG. 4 illustrates a flow diagram of the method of the present invention.

2. an ROI definition module 302—defining an ROI by selecting a voxel subset from the input data, wherein the definition of the ROI for the input function makes use of one of the strategies selected from the group consisting of the following:
  a. a voxel selection component 302.*a*—electing all voxels that are similar to the "reference input TAC" within, e.g., a much coarser predefined ROI 303;
  b. a voxel clustering component 302.*b*—voxel clustering, wherein, referring to FIG. 4, the selection of the cluster is according to a technique selected from the group consisting of being most similar to the "reference input TAC" 302.*b.i* and integrating the similarity to the "reference input TAC" in the clustering process 302.*b.ii* (see, e.g., M. Liptrot, et. al., "Cluster Analysis in Kinetic Modeling of the Brain: A Non-Invasive Alternative to Arterial Sampling," *Neuroimage*, vol. 21, pp. 483-491, 2004); and
  c. a voxel region-growing component 302.*c*—region-growing from the best matching voxel(s).

Figure 1:
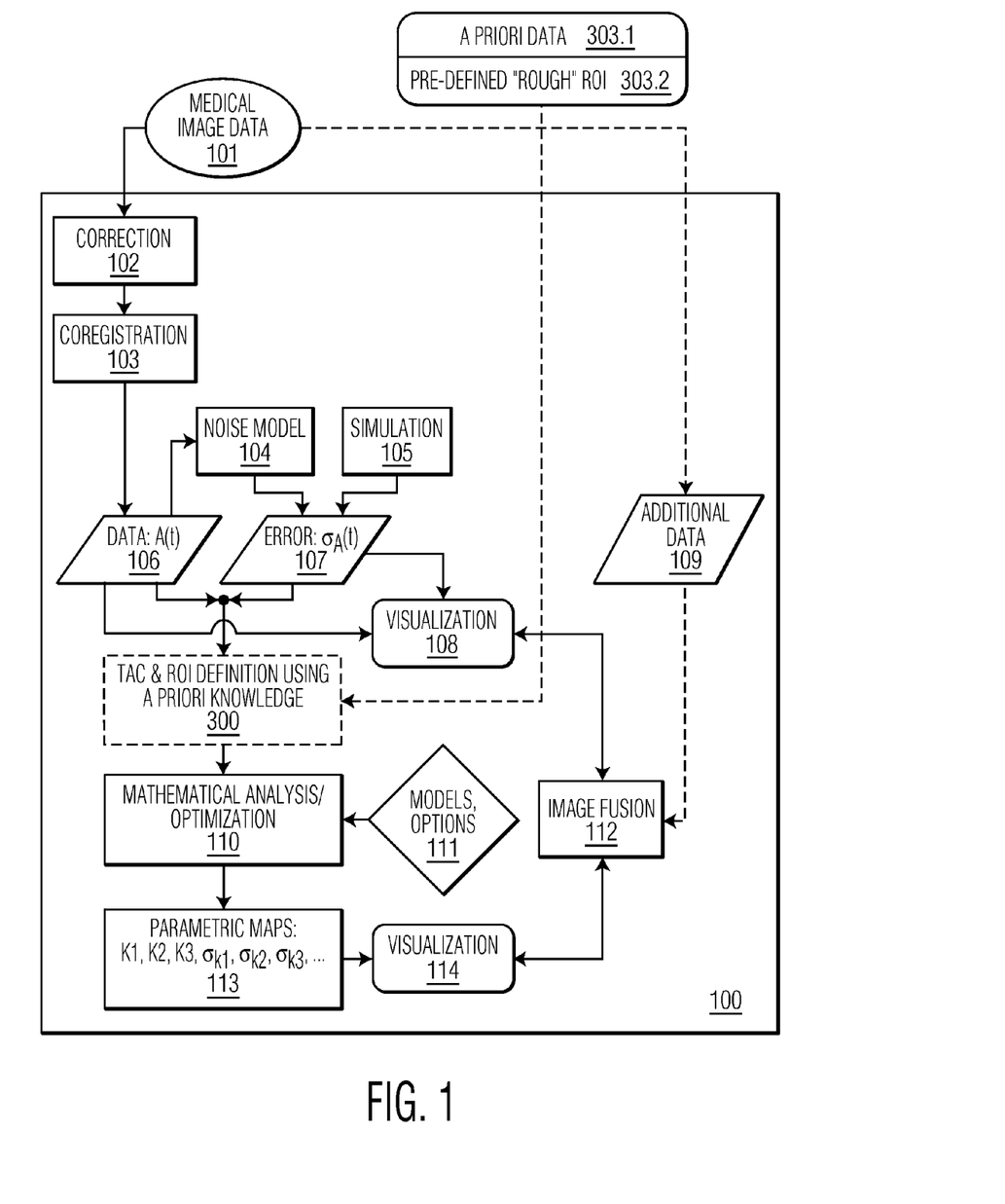
FIG. 1 illustrates an image analysis system modified to define an ROI according to the present invention.
Figure 2A:
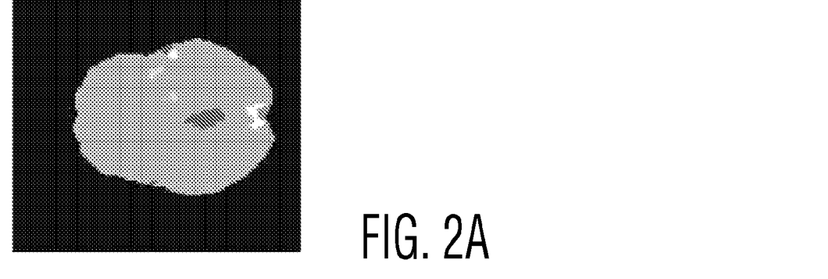
FIG. 2 illustrates clustering applied to a PET image.
Figure 2B:
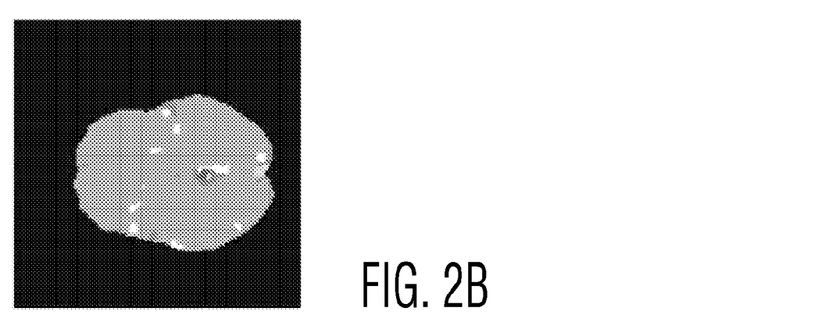
Figure 2C:
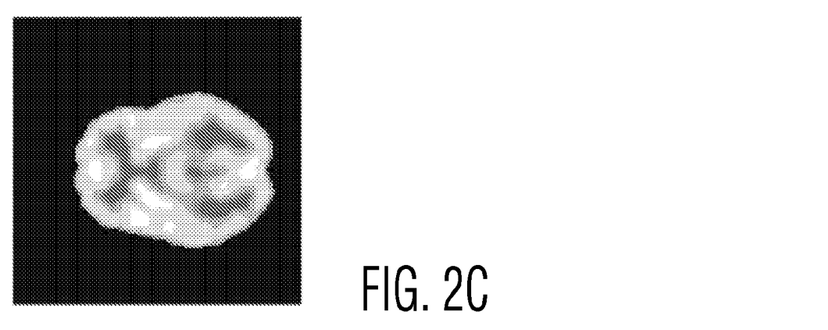
Figure 2D:
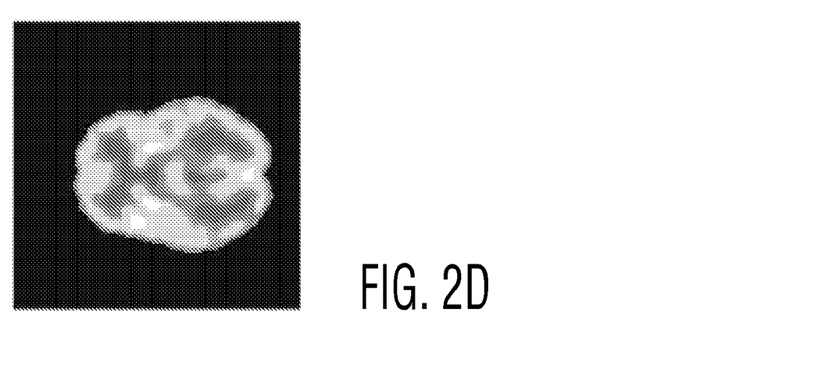

An image analysis system typically has as input the full set of recorded images (the 4-dimensional time series of scans) and generates from this input maps of all the relevant chemical, biological and physiological parameters on a required per-voxel basis. For example, in a preferred embodiment of a system that includes the present invention, this is achieved by the system illustrated in FIG. 1:

1. Data acquisition and pre-processing:
  a. Transfer of the input medical image data 101 (static/dynamic time series) from a medical imaging device to the apparatus modified 300 according to the present invention;
  b. Data correction (e.g. partial volume effects, etc.) 102;
  c. Co-registration of different data subsets (e.g., different time frames or data from different modalities) 103; and
  d. Calculation of error data sets 107 from the input data 106 either by means of a noise model 104 or by a simulation 105 incorporating aspects such as, e.g., geometry and hardware specifications of the medical-imaging device.
2. Visualization 108 of the input data 106 and the error data 107 of the input data 106;
3. Selection of a region-of-interest (ROI) according to the present invention 300 with optional specification of a pre-defined "rough" ROI 303;
4. Mathematical Analysis 110:
  a. Selection of a compartment model from a list containing multiple alternatives;
  b. Specification of model parameters: start value, lower and upper bounds, additional fixed parameters;
  c. Selection of an analysis method: per-voxel within ROI (one pass/multipass with at first low and then increasing resolution) or regional (average of ROI);
  d. Selection of the optimization method 111 (e.g., Levenberg-Marquard, Gauss-Newton, Simplex);
  e. Analytical solution of the underlying differential equations of the compartment model and, if necessary, analytical computation of the gradients with respect to the model parameters 110; and
  f. Optimization of the solutions with respect to the relevant parameters (specified under a and b) using a weighted least squares fit to the input data;
5. Storage of the final result of the optimization, parameter-error estimates and statistical information ($\chi^2$/d.o.f., correlation matrix, etc.) where "d.o.f.". is degrees of freedom; and
6. Visualization of results 108-?114:
  a. Visualization 114 of parametric maps 113 of all relevant parameters,
  b. Possibility to fuse the maps with additional medical images (e.g. anatomical CT scans) 112; and
  c. Visualization 108 of the resulting model curve (e.g., time activity curve for dynamic scans) using the optimized set of parameters superimposed 110 on the input data.

The system of FIG. 1 includes the present invention and performs all steps starting from transfer of the input medical-image data 101, e.g., from a medical-imaging device in real-time or from a storage device, to visualization 108 and 114 of the results. Such an integrated system has the advantage that the data need not be converted multiple times between various formats for each processing step. Visualization 114 of the resulting parametric maps and fusing 112 with additional information 109 can also be performed using the same system.

The present invention is applicable to all image-analysis products that employ pharmacokinetic modeling for enhanced analysis based on dynamic acquisition procedures as well as non-dynamic acquisition procedures, e.g., after-the-exam confirmatory analyses. The present invention may be an apparatus, e.g., a functionally dedicated 1C, or a software module bundled with the image-analysis machine or may be sold as a stand-alone system.

While the preferred embodiments of the present invention have been illustrated and described, it will be understood by those skilled in the art that the system, apparatus and method as described herein are illustrative, and various changes and modifications may be made and equivalents may be substituted for elements thereof without departing from the true scope of the present invention. In addition, many modifications may be made to adapt the teachings of the present invention to a particular medical imaging set up without departing from its central scope. Therefore, it is intended that the present invention not be limited to the particular embodiments disclosed as the best mode contemplated for carrying out the present invention, but that the present invention include all embodiments falling with the scope of the appended claims.

The invention claimed is:
1. A method using a priori data for a non-invasive input function definition to a pharmacokinetic modeling procedure, comprising the acts of:
receiving a medical image;
providing the a priori data that describes at least one attribute of the received medical image;

with the provided a priori data and for the received medical image, computing a reference input time-of-activity curve (TAC) having at least one major parameter; and defining the input function to the pharmacokinetic modeling procedure using the computed reference input, wherein a region-of-interest (ROI) definition module receives the computed reference input TAC;

wherein the defining act comprises the acts of:

identifying best-matching voxels of the received medical image that best match the computed TAC;

region-growing using the identified best-matching voxels to automatically define at least one ROI.

2. The method of claim 1, wherein the defining act further comprises the acts of:

determining whether the computed TAC is both computable and accurate using a pre-determined accuracy criterion; and when it is determined that the computed TAC is both computable and accurate, the defining act defines the computed TAC as the input function to the pharmacokinetic modeling procedure;

otherwise, the defining act uses the computed TAC to define a region-of-interest (ROI) as the input function to the pharmacokinetic modeling procedure.

3. The method of claim 2, wherein the a priori data comprises at least one item selected from the group consisting of a set of tracer characteristics and administered dose, patient weight and blood volume, and a set of medical-imaging-device characteristics.

4. The method of claim 3, wherein the at least one major parameter is selected from the group consisting of peak size and width and tail size and width.

5. The method of claim 1, wherein the identifying act further comprises selecting best-matching voxels based on a pre-determined distance measurement between a voxel and the computed TAC.

6. The method of claim 5, wherein the a priori data comprises at least one item selected from the group consisting of a set of tracer characteristics and administered dose, patient weight and blood volume, and a set of medical-imaging-device characteristics.

7. The method of claim 6, wherein the a priori data further comprises a pre-defined ROI as the identified best-matching voxels in the region-growing act.

8. The method of claim 7, further comprising the act of checking the defined ROI using the computed TAC as a post diagnostic.

9. The method of claim 6, wherein the distance measure is selected from the group consisting of Manhattan distance, Euclidean distance, weighted Manhattan distance, and weighted Euclidean distance.

10. The method of claim 9, further comprising the act of checking the defined ROI using the computed TAC as a post diagnostic.

11. An apparatus for a non-invasive input function definition to a pharmacokinetic modeling procedure, comprising:

a reference input TAC computation module that computes a reference input TAC based on received medical-image data including a priori data;

a region-of-interest (ROI) definition module that receives the computed reference input TAC and defines an ROI based thereon; and a processor configured to define the input function to the pharmacokinetic modeling procedure using the computed reference input TAC by identifying best-matching voxels of the received medical image that best match the computed TAC, and region-growing using the identified best-matching voxels to automatically define at least one ROI.

12. A system for medical-image analysis, comprising:

a data acquisition pre-processing module that acquires a medical-image data, corrects and co-registers the acquired data, and calculates error data sets therefrom to produce a processed input-image data set;

an apparatus that non-invasively defines an input function from the produced input-image data set; and a pharmacokinetic modeling subsystem that accepts the input function and models the data therewith, wherein the apparatus comprises:

a reference input TAC computation module that computes a reference input TAC based on received medical-image data including a priori data;

a region-of-interest (ROI) definition module that receives the computed reference input TAC and defines an ROI based thereon; and a processor configured to define the input function to the pharmacokinetic modeling procedure using the computed reference input TAC by identifying best-matching voxels of the received medical image that best match the computed TAC, and region-growing using the identified best-matching voxels to automatically define at least one ROI.

* * * * *